(12) United States Patent
Speziali

(10) Patent No.: US 6,916,338 B2
(45) Date of Patent: Jul. 12, 2005

(54) SYNTHETIC LEAFLETS FOR HEART VALVE REPAIR OR REPLACEMENT

(75) Inventor: Giovanni Speziali, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 0 days.

(21) Appl. No.: 10/471,940

(22) PCT Filed: Mar. 15, 2002

(86) PCT No.: PCT/US02/07976

§ 371 (c)(1),
(2), (4) Date: Sep. 16, 2003

(87) PCT Pub. No.: WO02/074201

PCT Pub. Date: Sep. 26, 2002

(65) Prior Publication Data

US 2004/0088046 A1 May 6, 2004

Related U.S. Application Data

(60) Provisional application No. 60/276,008, filed on Mar. 16, 2001.

(51) Int. Cl.$^7$ .................................................. A61F 2/06
(52) U.S. Cl. .................................... 623/2.12; 623/2.19
(58) Field of Search .............................. 623/2.11–2.42

(56) References Cited

U.S. PATENT DOCUMENTS

| | | | | |
|---|---|---|---|---|
| 6,102,944 A | * | 8/2000 | Huynh et al. | 623/2.14 |
| 6,139,575 A | | 10/2000 | Shu et al. | |
| 6,171,335 B1 | * | 1/2001 | Wheatley et al. | 623/2.17 |
| 6,338,740 B1 | * | 1/2002 | Carpentier | 623/2.13 |
| 6,695,879 B2 | * | 2/2004 | Bell | 623/2.41 |

* cited by examiner

Primary Examiner—Thomas Barrett
(74) Attorney, Agent, or Firm—Fish & Richardson P.C., P.A.

(57) ABSTRACT

Heart valve leaflets (10) are described that include a plurality of supports (350) within a coapting portion (20) and a substantially arcuate portion (30). The plurality of supports (350) provide the leaflet (10) with anisotropic elasticity.

4 Claims, 4 Drawing Sheets

SYNTHETIC LEAFLETS FOR HEART VALVE REPAIR OR REPLACEMENT

This application is a National Stage Application under 35 U.S.C. §371 that claims the benefit of application Ser. No. PCT/US02/07976, filed Mar. 15, 2002, which claims the benefit of U.S. Provisional Application Ser. No. 60/276,008, filed Mar. 16, 2001.

TECHNICAL FIELD

This invention relates to heart valves, and more particularly to heart valves containing synthetic heart valve leaflets with improved strength, flexibility, and durability.

BACKGROUND

Prosthetic heart valves are used to replace damaged or diseased heart valves, including the aortic, mitral (bicuspid), tricuspid, and pulmonary heart valves. There are two basic types of prosthetic heart valves, mechanical and tissue-type valves. Mechanical heart valves use a pivoting mechanical closure to provide unidirectional blood flow, while tissue type valves are made from natural tissue valve leaflets. Mechanical valves are made of pyrolytic carbon, and although they do not wear out, the patient in which the valve is implanted requires life-long anticoagulation, which is associated with an increased incidence of thrombotic and hemorrhagic complications. Tissue valves resemble native valves, and do not require life-long anticoagulation, but they wear out over time (in general after about 10 years). In fact, the tissue they are made of is a simple, flat piece of pericardium, and does not possess the structural characteristics necessary for long-term durability. Other types of tissue valves utilize animal valves, but the natural (dead) tissues degrade and calcify over time. Thus, there is a continued need for heart valves with improved functional properties.

SUMMARY

The invention is based on heart valve leaflets with improved functional and structural characteristics. In particular, heart valve leaflets of the invention contain a plurality of stress-bearing supports, which resemble the disposition of collagen fibers in the native aortic valve and allow elastic stretching in the circumferential direction with minimal elastic stretching in the radial direction. This property is called anisotropic elasticity. More particularly, the supports allow up to 50–70% elastic stretching in the circumferential direction but only 10–15% in the radial direction. In addition, the heart valve leaflets include a central thickening about the free edge of the leaflet, which, during closure of the valve, coapts with the other leaflets' central thickenings. This central thickening provides additional structural support to the stress-bearing supports, and helps reduce the systo-diastolic movement of the leaflets necessary to obtain coaptation, reducing overall mechanical stress and wear on the valve. Leaflets described herein have longer durability because of the unique structural characteristics, but do not require lifelong anticoagulation because of its design and flow dynamics. The heart valve leaflets of the invention can be used to replace a damaged leaflet or to construct stented or stentless heart valves.

In one aspect, the invention features a synthetic heart valve leaflet that includes a coapting portion having a free edge; a substantially arcuate portion adjacent the coapting portion and having a peripheral edge; and a plurality of supports within the coapting portion and the substantially arcuate portion that provide the leaflet with anisotropic elasticity. A region about the mid-line of the coapting portion has a thickness greater than the thickness of at least one other region of the leaflet. The coapting portion and the substantially arcuate portion can extend between a pair of opposing tabs. The elasticity of the leaflet in a circumferential direction can be greater than the elasticity in a radial direction, wherein the circumferential direction is from the coapting edge to the peripheral edge, and wherein the radial direction is perpendicular to the circumferential direction. The leaflet can be composed of a material selected from the group consisting of a biocompatible fabric and a biocompatible polymer. The biocompatible polymer can be a polyurethane.

In another aspect, the invention features a synthetic heart valve leaflet comprising a pair of opposing tabs; a coapting portion extending between the pair of opposing tabs and having a free edge; a substantially arcuate portion adjacent the coapting portion and having a peripheral edge; and a plurality of supports extending between the pair of opposing tabs, wherein the plurality of supports provide the leaflet with anisotropic elasticity, wherein a region about the mid-line of the coapting portion has a thickness greater than the thickness of at least one other region of the leaflet. The region of greater thickness can include a movement tracking component (e.g., a magnetically active particle).

Each support of the plurality of supports can be increasingly arcuate from the coapting edge to the peripheral edge. At least two supports of the plurality can extend from one tab of the pair of opposing tabs to the region of greater thickness. The plurality of supports can be fibers. Each support of the plurality of supports can include a region of the leaflet having a thickness greater than the thickness of adjacent regions of the leaflet. The thickness of the peripheral edge can be greater than the thickness of the substantially arcuate portion. The leaflet can be composed of a material selected from the group consisting of a biocompatible fabric and a biocompatible polymer.

The invention also features prosthetic heart valves. The heart valves include a plurality of leaflets described above, wherein each leaflet is attached to each other leaflet of the plurality (e.g., attached to one tab of each of the other two leaflets). The heart valve further can include a stent, wherein each leaflet is attached to the stent.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description and from the claims.

DESCRIPTION OF DRAWINGS

Like reference symbols in the various drawings indicate like elements.

DETAILED DESCRIPTION

Figure 1:
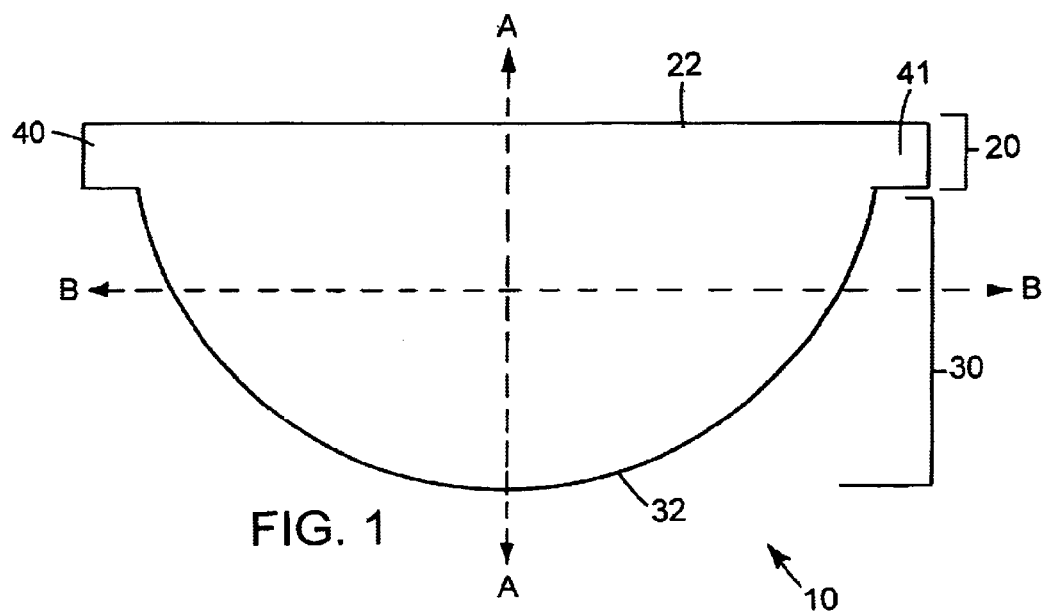
FIG. 1 is a perspective view of a heart valve leaflet with anisotropic elasticity.

Referring to FIG. 1, a synthetic heart valve leaflet 10 is shown that has anisotropic elasticity. Leaflet 10 includes a coapting portion 20 having a free edge 22. A substantially arcuate portion 30 is adjacent to coapting portion 20, and includes a peripheral edge 32. Typically, leaflet 10 is made of an elastic, biocompatible polymer, and has elasticity in two directions, designated A and B in FIG. 1, with elasticity in the A direction greater than the elasticity in the B direction, although the elasticity profile of the leaflet may be adapted as necessary for a particular application. Elasticity in the A direction is referred to as the circumferential direction, and is from the free edge to the peripheral edge, while elasticity in the B direction is referred to as the radial direction, and is perpendicular to the circumferential direction.

Figure 2:
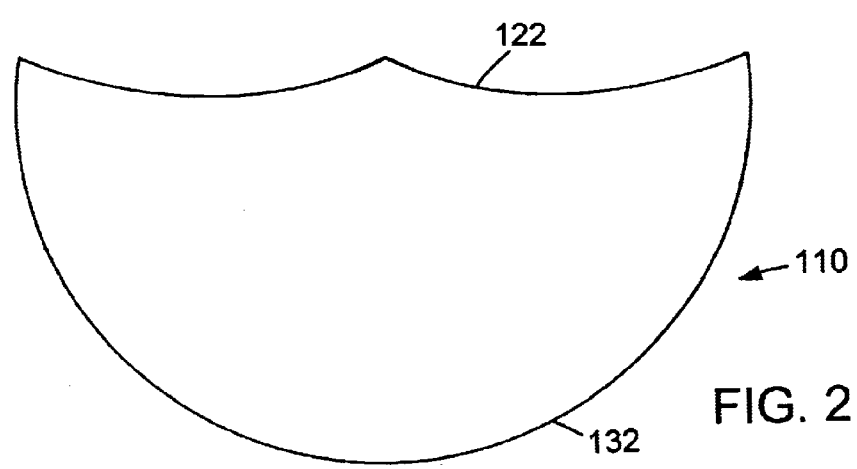
FIG. 2 is a perspective view of a heart valve leaflet having a scalloped edge.

In the embodiment depicted in FIG. 1, leaflet 10 optionally has a pair of opposing tabs 40 and 41. The coapting portion 20 and the substantially arcuate portion 30 extend between the opposed tabs 40, 41. Although the free edge 22 is linear in FIG. 1, the profile of free edge 22 can be altered, e.g., free edge 22 can be scalloped and form a midpoint peak (see leaflet 110 in FIG. 2 with scalloped free edge 122 and peripheral edge 132). The peripheral edge 32 is the area that can be attached directly to a vessel wall (e.g., the aortic wall) or to a supporting structure (e.g., prosthetic heart valve strut). Peripheral edge 32 can be the same thickness as the leaflet 10 or can be thicker to facilitate attachment of the peripheral edge 32 to the vessel wall or supporting structure.

Figure 3A:
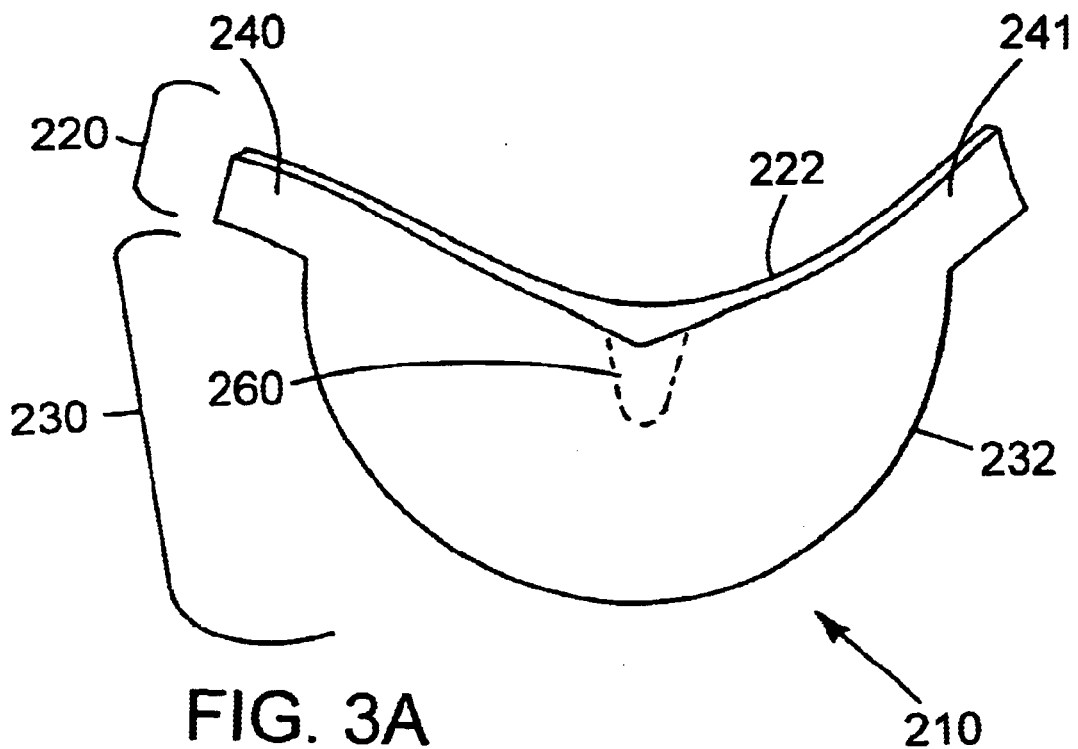
FIG. 3A is a perspective view of a heart valve containing a thickening about the mid-line of the leaflet and a plurality of supports.
Figure 3B:
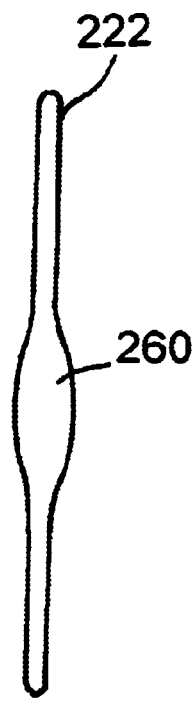
FIG. 3B is an edge view of the leaflet of FIG. 3A taken along line B—B of FIG. 3A.

The thickness of the leaflet may be varied in one region or in multiple regions as necessary to provide a specific elasticity profile for a particular application. The variable thickness gradient of the leaflet may also be combined with an arrangement of supports to provide the leaflet with a desired elasticity profile. Referring to FIG. 3A, a region 260 of the leaflet 210, which is located about midway between the tabs 240, 241 along the free edge 222, has a thickness different from at least one other region of the leaflet 210. FIG. 3B provides a view of this thickening along the free edge 222 of FIG. 3A. In the embodiment shown in FIG. 3A, the thickened region 260 extends from the coapting portion 220 into the substantially arcuate portion 230 and has a generally semicircular or drop-like shape. The region 260 may also be referred to as a "central thickening."

Figure 4A:
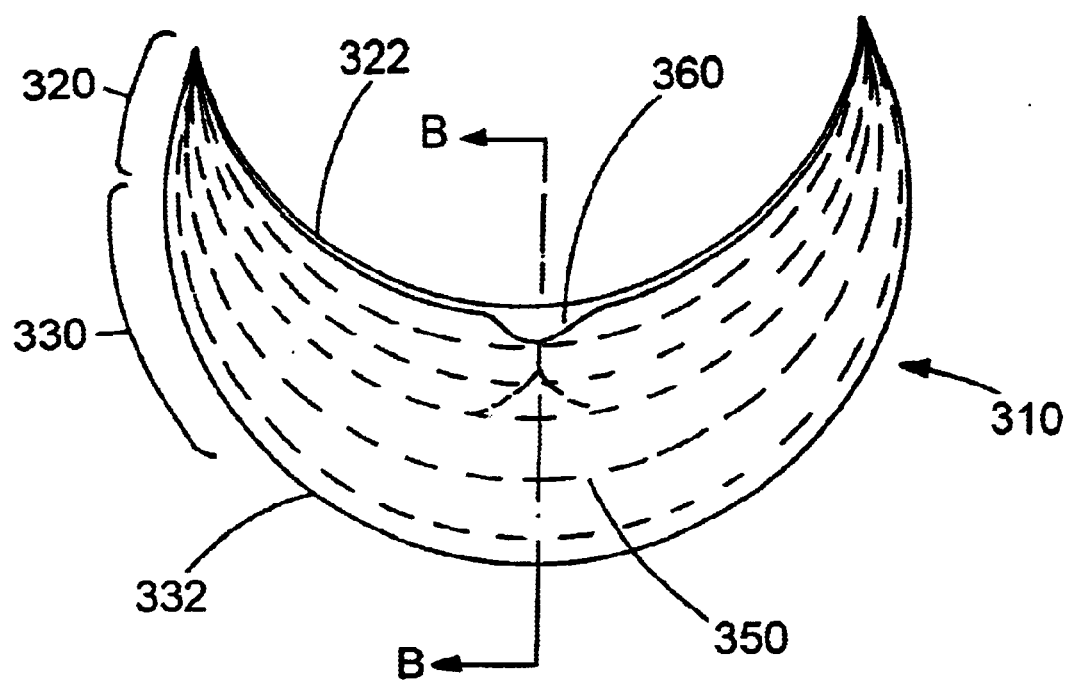
FIG. 4A is a perspective view of a heart valve leaflet containing a thickening about the mid-line of the leaflet, and supports anchored in the thickening.
Figure 4B:
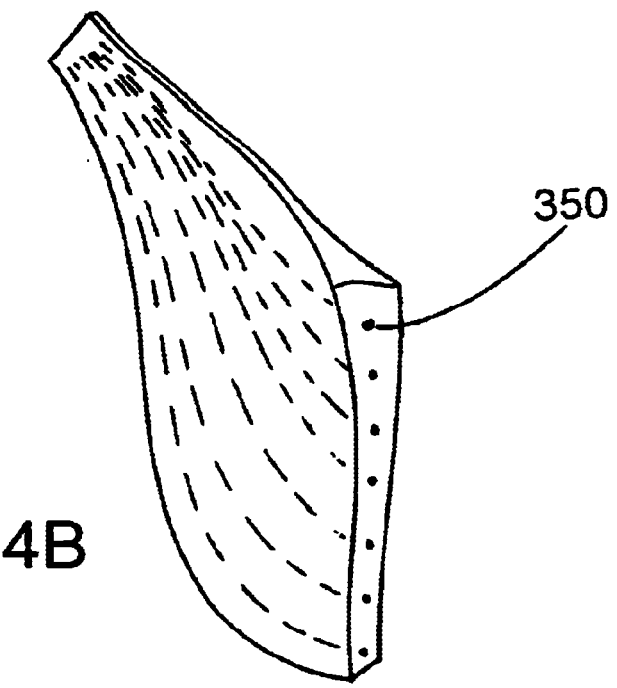
FIG. 4B is a cross-section taken along line B—B of FIG. 4A.

In another embodiment, a leaflet can contain a plurality of rib-like supports within a coapting portion and a substantially arcuate portion. The supports provide the leaflet with anisotropic elasticity. The supports may be shaped and positioned in any region between a peripheral edge of the arcuate portion and a free edge of the coapting portion as necessary to provide a specific elasticity profile for the leaflet. For example, as indicated in FIG. 4A, the plurality of supports can be embedded within the coapting portion 320 and substantially arcuate portion 330 of leaflet 310. Each support 350 can be increasingly arcuate from the free edge 322 to the peripheral edge 332, while reaching from commissure to commissure. FIG. 4B provides a view of the embedded supports along line B—B of FIG. 4A. A central thickening region 360 can provide an anchor point for at least one (e.g., two or three) of a plurality of individual supports 350. This arrangement reduces the radial elasticity throughout the leaflet surface.

Figure 5:
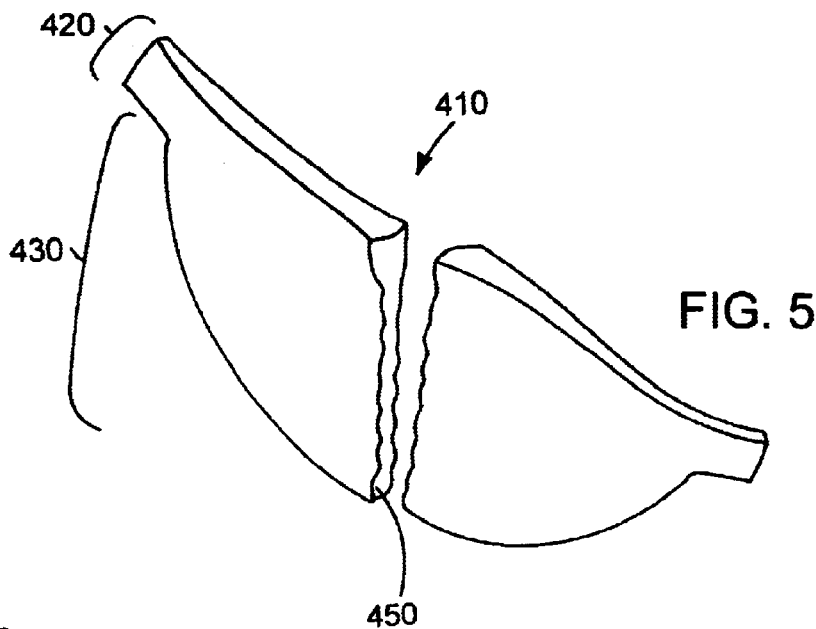
FIG. 5 is a view of a heart valve leaflet having regions of different thicknesses.

In an alternate embodiment shown in FIG. 5, the supports 450 of the leaflet 410 are regions of the coapting portion 420 and substantially arcuate portion 430 that have a thickness that differs from adjacent regions. The thickness may be greater or less than adjacent regions, depending on the composition of the leaflet.

A movement-tracking component can optionally be embedded within the central thickening region, providing a non-invasive method for tracking and reconstructing the movement of each valve leaflet in vivo. Movement-tracking components can help determine if the valve is functioning appropriately. Non-limiting examples of tracking components include magnetically active particles and sensors. For example, the movement of a leaflet containing a magnetic particle can be monitored in vivo by magnetic field tracking.

Figure 6:
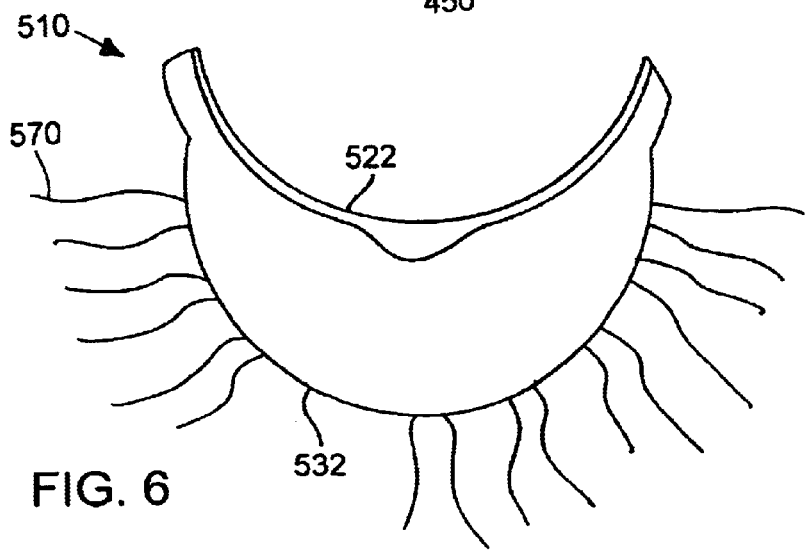
FIG. 6 is a perspective view of a heart valve leaflet contains a plurality of pre-attached sutures.

Referring to FIG. 6, a plurality of sutures 570 can be optionally pre-attached to the peripheral edge 532 of a leaflet 510. The sutures can be evenly spaced around peripheral edge 532. One or more surgical needles (not shown in FIG. 6) can be attached to the sutures to assist the surgeon in attaching the leaflet to the vessel wall. Pre-attachment of the sutures during the manufacturing process can minimize the introduction of micro-fractures on the leaflet surface. Micro-fractures can allow calcium ions to be deposited within the leaflet, forming 'spikes' that further increase tissue wear and tear to final breakdown.

The leaflet is composed of one or more biocompatible, elastomeric materials, such as a biocompatible polymer, fiber, or fabric. Non-limiting examples of biocompatible polymers include polyurethanes such as polyether polyurethane, and silicones. The biocompatible material also can be radio-opaque. In one embodiment, the supports are composed of a biocompatible polymer such as polytetrafluoroethylene (PTFE) and another biocompatible polymer is used to form the coapting and substantially arcuate is portions of the leaflet. Such supports can reduce elasticity in the radial direction because the supports (e.g., fibers) are made of a biocompatible material with limited elastic properties.

In other embodiments, the supports and the coapting and substantially arcuate portions are composed of the same biocompatible polymer. For example, the supports can be ridges in the leaflet that have a thickness greater than that of adjacent regions of the leaflet (see, for example, FIG. 5).

Individual leaflets can be formed by molding or casting. Alternatively, molding or casting can be used to produce a heart valve containing a plurality of leaflets. Regions of the leaflet having different thicknesses can be formed in the initial manufacture or by subsequent processing.

In other embodiments, the leaflet can be woven from a biocompatible fabric in which the elasticity of fibers extending in the radial direction is less than the elasticity of the fibers extending in the circumferential direction.

The leaflet can be treated (e.g., impregnated or coated) with an anticoagulant such as heparin to minimize blood clotting in vivo. In addition, the leaflet can be treated with a compound to reduce the permeability of the leaflet to calcium. Continuous movement of a heart valve can cause micro-fractures in the leaflet surface, which, as indicated above, allows calcium ions to be deposited within the leaflet, forming 'spikes' that further increase tissue wear and tear to final breakdown.

Leaflets of the invention can be used to produce synthetic heart valves for replacing the aortic, bicuspid, tricuspid, or pulmonary valves. Accordingly, the dimensions and shape of the leaflet can vary depending on the size and shape of the valve to be replaced. A plurality of leaflets can be used to form prosthetic heart valves according to established methodologies. See, for example, U.S. Pat. No. 6,102,944. For example, two or three leaflets can be attached to a generally circular supporting wire frame or stent to provide a support structure, which imparts a degree of controlled flexibility and reduces stress on the leaflets during valve closure. More particularly, the peripheral edge of each of the leaflets can be sewn, adhered, bonded, or fused to a supporting wire frame or stent. In embodiments in which the leaflet contains a pair of opposing tabs (See, for example, tabs 40, 41 in FIG. 1), each leaflet also can be attached to one tab of each of the other leaflets, to further secure the leaflets to each other.

Figure 7:
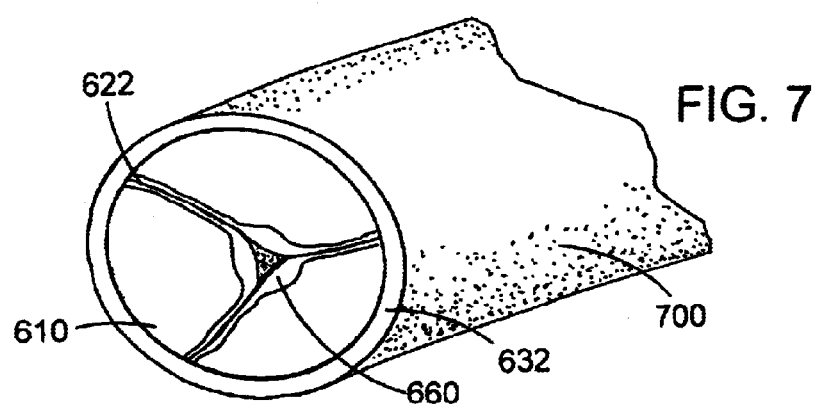
FIG. 7 is a view of a prosthetic heart valve containing three leaflets.

For example, referring to FIG. 7, after attaching a peripheral edge 632 of the leaflet 610 to a support 700 (e.g., a stent), a free edge 622 of each leaflet remains unattached, and coapts (i.e., meets) with the coapting portion and free edge of each of the other leaflets. Central thickening 660 allows for central coaptation to occur with less central stretching and bending of the leaflet, reducing structural stress of the leaflet.

While the support 700 is depicted as being a tube, suitable wire frames or stents are available in many shapes and sizes. For example, the wire frame or stent can have a plurality of upstanding commissures or posts to which each leaflet can be attached. Supporting wire frames or stents also can be covered with a biocompatible material that provides an attachment point for the leaflet peripheral edge. Furthermore, the wire frame or stent can have a sewing ring attached around its periphery to facilitate suturing of the prosthetic heart valve to the natural annulus.

A number of embodiments of the invention have been described. Nevertheless, it will be understood that various modifications may be made without departing from the spirit and scope of the invention. Accordingly, other embodiments are within the scope of the following claims.

What is claimed is:

1. A synthetic heart valve leaflet comprising:
   a) coapting portion having a free edge;
   b) a substantially arcuate portion adjacent said coapting portion, said arcuate portion having a peripheral edge; and
   c) a plurality of supports within said coapting portion and said substantially arcuate portion, wherein said plurality of supports provide said leaflet with anisotropic elasticity, and wherein a region about the mid-line of said coapting portion has a thickness greater than the thickness of at least one other region of said leaflet, wherein said plurality of supports is composed of polytetrafluoroethylene.

2. A synthetic heart valve leaflet comprising:
   a) a pair of opposing tabs;
   b) a coapting portion extending between said pair of opposing tabs and having a free edge;
   c) a substantially arcuate portion adjacent said coapting portion and having a peripheral edge; and
   d) a plurality of supports extending between said pair of opposing tabs, wherein said plurality of supports provide said leaflet with anisotropic elasticity, and wherein a region about the mid-line of said coapting portion has a thickness greater than the thickness of at least one other region of said leaflet, wherein each support of said plurality of supports is increasingly arcuate from said coapting edge to said peripheral edge.

3. A synthetic heart valve leaflet comprising:
   a) a pair of opposing tabs;
   b) a coapting portion extending between said pair of opposing tabs and having a free edge;
   c) a substantially arcuate portion adjacent said coapting portion and having a peripheral edge; and
   d) a plurality of supports extending between said pair of opposing tabs, wherein said plurality of supports provide said leaflet with anisotropic elasticity, and wherein a region about the mid-line of said coapting portion has a thickness greater than the thickness of at least one other region of said leaflet, wherein said region of a greater thickness contains a movement-tracking component, and wherein said movement-tracking component is a magnetic particle.

4. A synthetic heart valve leaflet comprising:
   a) pair of opposing tabs;
   b) a coapting portion extending between said pair of opposing tabs and having a free edge;
   c) a substantially arcuate portion adjacent said coapting portion and having a peripheral edge; and
   d) a plurality of supports extending between said pair of opposing tabs, wherein said plurality of supports provide said leaflet with anisotropic elasticity, and wherein a region about the mid-line of said coapting portion has a thickness greater than the thickness of at least one other region of said leaflet, wherein the thickness of said peripheral edge is greater than the thickness of said substantially arcuate portion.

* * * * *

UNITED STATES PATENT AND TRADEMARK OFFICE
CERTIFICATE OF CORRECTION

PATENT NO. : 6,916,338 B2
DATED : July 12, 2005
INVENTOR(S) : Giovanni Speziali

It is certified that error appears in the above-identified patent and that said Letters Patent is hereby corrected as shown below:

Column 5,
Line 53, before "coapting" insert -- a --;

Column 6,
Line 41, before "pair" insert -- a --.

Signed and Sealed this

Fourteenth Day of March, 2006

JON W. DUDAS
*Director of the United States Patent and Trademark Office*